United States Patent [19]
Arvidsson et al.

[11] Patent Number: 5,773,712
[45] Date of Patent: Jun. 30, 1998

[54] METHOD FOR MEASURING VISCOSITY AND VISCOSIMETER

[75] Inventors: Thomas Arvidsson, Hamneda; Pierre Ståhl, Lammhult, both of Sweden

[73] Assignee: Glasforskningsinstitutet, Växjö, Sweden

[21] Appl. No.: 809,109

[22] PCT Filed: Sep. 12, 1995

[86] PCT No.: PCT/SE95/01024

§ 371 Date: Apr. 28, 1997

§ 102(e) Date: Apr. 28, 1997

[87] PCT Pub. No.: WO96/08709

PCT Pub. Date: Mar. 21, 1996

[30] Foreign Application Priority Data

Sep. 13, 1994 [SE] Sweden .................................. 9403039

[51] Int. Cl.⁶ .................................................. G01N 11/14
[52] U.S. Cl. ........................................ 73/54.28; 73/54.32
[58] Field of Search ............................... 73/54.28, 54.29, 73/54.31, 54.32, 54.33, 54.34, 54.35

[56] References Cited

U.S. PATENT DOCUMENTS

| 722,576 | 3/1903 | Grand ..................................... | 73/54.28 |
| 3,115,769 | 12/1963 | Bowen, Jr. ............................. | 73/54.32 |
| 3,162,038 | 12/1964 | Roberson et al. ..................... | 73/54.35 |
| 3,803,903 | 4/1974 | Lin ..................................... | 73/54.28 X |
| 5,503,003 | 4/1996 | Brookfield ......................... | 73/54.28 X |
| 5,531,102 | 7/1996 | Broofield et al. ................. | 73/54.28 X |

OTHER PUBLICATIONS

Derwent's Abstract, No. G2039 D/27, Abstract of SU 761,882, Sep. 7, 1980.

*Primary Examiner*—Michael Brock
*Attorney, Agent, or Firm*—Shapiro and Shapiro

[57] ABSTRACT

A method for measuring viscosity and a viscosimeter are disclosed. Thus, a rotary measuring head (3) is introduced into a liquid (1), and the torque exerted on the measuring head (3) is sensed. The measuring head (3) is rotated at a substantially constant speed, and the torque is sensed at two depths of introduction of the measuring head (3) into the liquid (1). The viscosity of the liquid (1) is then calculated on the basis of the change in torque between the two depths of introduction and the distance therebetween.

7 Claims, 3 Drawing Sheets

METHOD FOR MEASURING VISCOSITY AND VISCOSIMETER

BACKGROUND OF THE INVENTION

This invention concerns a method for measuring the viscosity of a liquid, wherein a rotary measuring head is introduced into the liquid, and the torque exerted on the measuring head is sensed. The invention further relates to a viscosimeter for implementing this method, said meter comprising a driving motor, which is provided with a torque sensor and is adapted to rotate a measuring head that is insertable into a liquid.

DESCRIPTION OF THE PRIOR ART

In many industrial processes, the viscosity of the liquids involved is of decisive importance to the practicability. A typical case is the production of glass containers, in which a liquid (here, of course, melted glass) is, in carefully adjusted batches, fed from a furnace through so-called feeder channels into a machine for blowing glass bottles. In spite of the fact that the viscosity of the melted glass is vital to the size and shape of the batches, as well as to the plasticity of the melted glass in the glass-blowing operation, no actual measurement of the viscosity of the melted glass is performed today. Instead, one confines oneself to determining the viscosity indirectly by sensing the temperature of the melted glass, optionally in combination with monitoring of the shape of the batch of melted glass cut off.

In an ongoing process, such a solution mostly yields satisfactory results, but in particular at start-up after an intermission or upon an alteration of e.g. the sort of glass (i.e. color or quality), an initial wastage of some size can hardly be avoided.

One reason for the absence of viscosity metering in today's production of glass containers, for instance, despite the obvious advantages offered by such metering, is that the prior-art measuring methods and viscosimeters are not suited for this purpose.

Amongst the prior-art viscosimeters, rotational viscosimeters are especially notable. The rotational viscosimeters comprise a motor which rotates a measuring head intended to be introduced in a given fashion into the liquid whose viscosity is to be determined. The viscosity is then actually determined by sensing the torque to which the measuring head is exposed when rotating in the liquid.

If reliable results are to be obtained, the rotational speed and the depth of introduction of the measuring head into the liquid have to be known, since these parameters naturally affect the torque, and hence the measurement results. Also, the position of the measuring head when introduced into the liquid has to be well-defined, since e.g. the side walls of the vessel holding the liquid also affect the torque. In the following, this effect will be referred to as the edge effect.

In a feeder channel of the type mentioned previously, it is not, however, possible to reliably determine either the depth of introduction of the measuring head or its position, partly because the analysed melted glass is in continuous movement, and partly because the melted glass gradually wears down the walls of the feeder channel, such that the flow conditions in the feeder channel undergo continuous change.

Quite apart from their limited practicability, the prior-art rotational viscosimeters are distinguished by the fact that much attention has to be given to the quality and the calibration of the torque meter (the offset of the torque meter has to be known), since but one value of the torque is obtained per measuring site for determining the viscosity.

SUMMARY OF THE INVENTION

In view of the failings of the prior art, a principal object of this invention is to provide a viscosity-measuring method obviating the drawbacks of the known methods, as well as a simple viscosimeter intended for the implementation of this method.

According to the invention, this object is achieved by a method which is of the type stated by way of introduction and which is characterised in that the measuring head is rotated at a substantially constant speed, that the torque is sensed at two depths of introduction of the measuring head into the liquid, and that the viscosity of the liquid is calculated on the basis of the change in torque between the two depths of introduction and the distance therebetween. Conveniently, the viscosimeter used for implementing this method is characterised in that the measuring head is circular-cylindrical and is adapted to be rotated about its cylinder axis as well as be introduced into the liquid along said axis and to an optional depth.

The method according to the invention, which thus does not use a measured value of a given depth of introduction but which uses the difference between two measured values at different and uncritical depths of introduction, thus provides, in a surprisingly simple manner, a highly reliable measure of the viscosity of the analysed liquid. Since, in addition, it is only the difference between the two measured values that is of interest here, the viscosimeter involved in the measurement may be of extremely simple design, and the torque may, for instance, be sensed with the aid of a simple angle transducer.

In a preferred mode of implementation of the method according to the invention, the measuring head is introduced into the liquid at a substantially constant speed, thus facilitating the definition of the distance covered between the two depths of introduction.

Finally, a preferred embodiment of the viscosimeter according to the invention is characterised in that the free end of the measuring head is rounded or conical, since this reduces both the cratering arising upon the initial introduction of the measuring head into the liquid, and the contribution by the end of the measuring head to the torque during the torque measurement.

BRIEF DESCRIPTION OF THE DRAWINGS

A preferred embodiment of the invention will now be described in more detail with reference to the accompanying drawings, in which.

DESCRIPTION OF A PREFERRED EMBODIMENT

Figure 1:
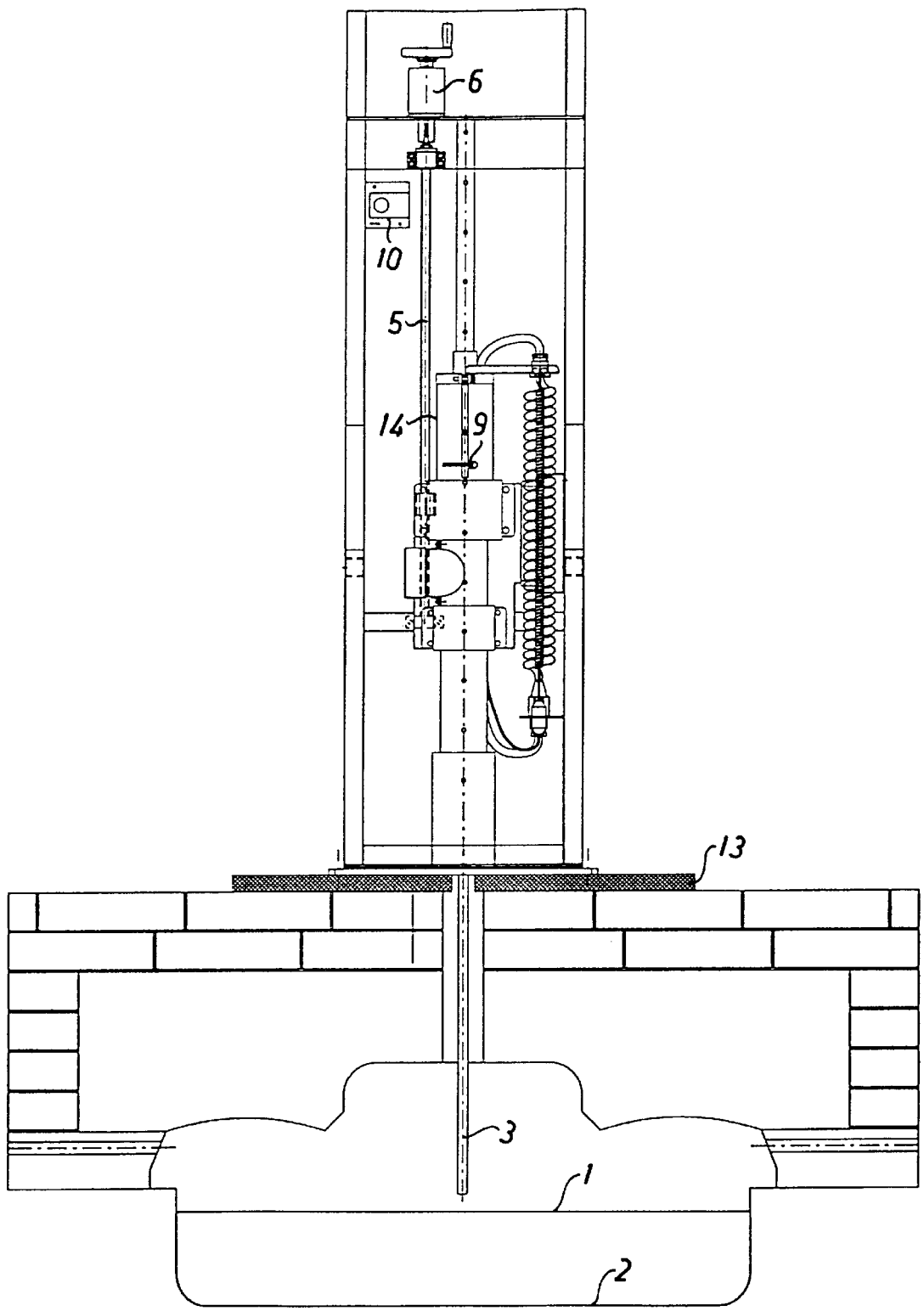
FIG. 1 shows in cross-section a feeder channel for melted glass and shows in partial cross-section an inventive viscosimeter arranged above the feeder channel.
Figure 2:
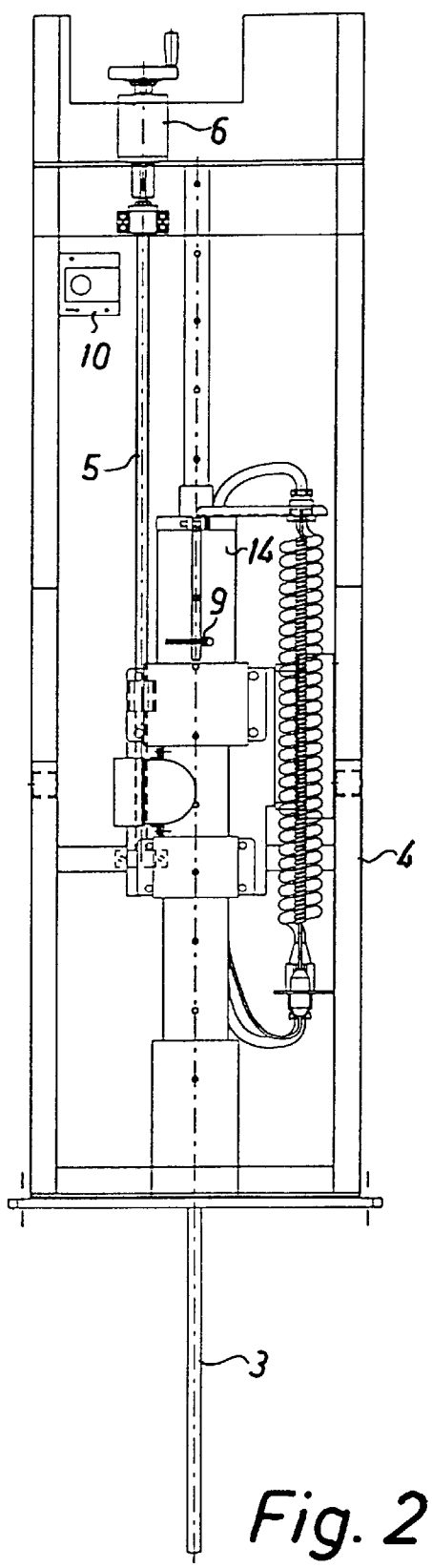
FIG. 2 shows the viscosimeter in FIG. 1 on a larger scale.
Figure 3:
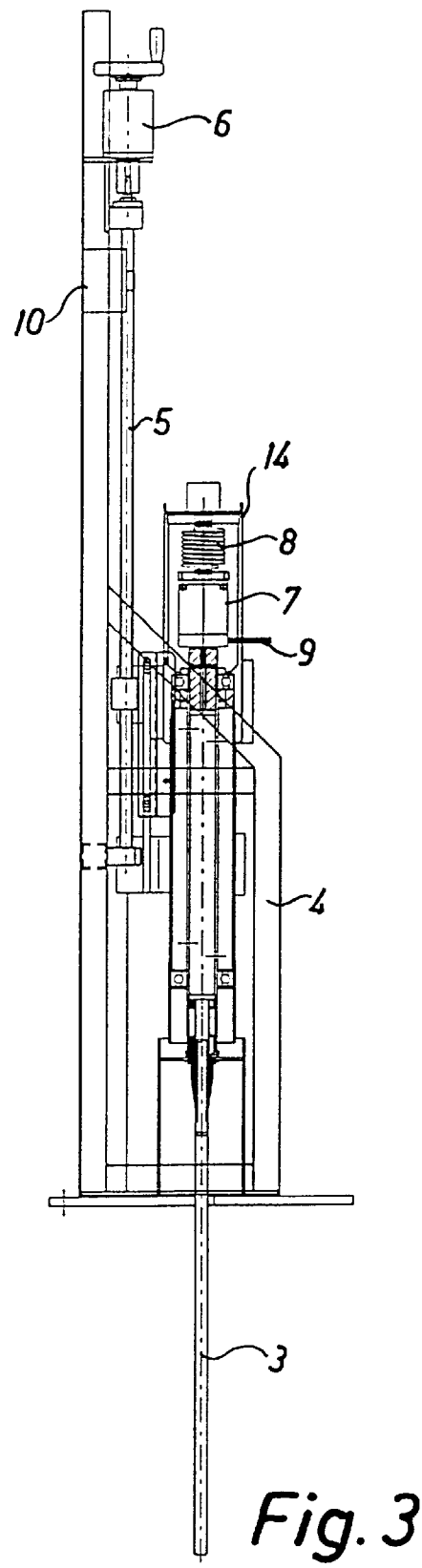
FIG. 3 shows the viscosimeter from the side and partly in section.
Figure 4:
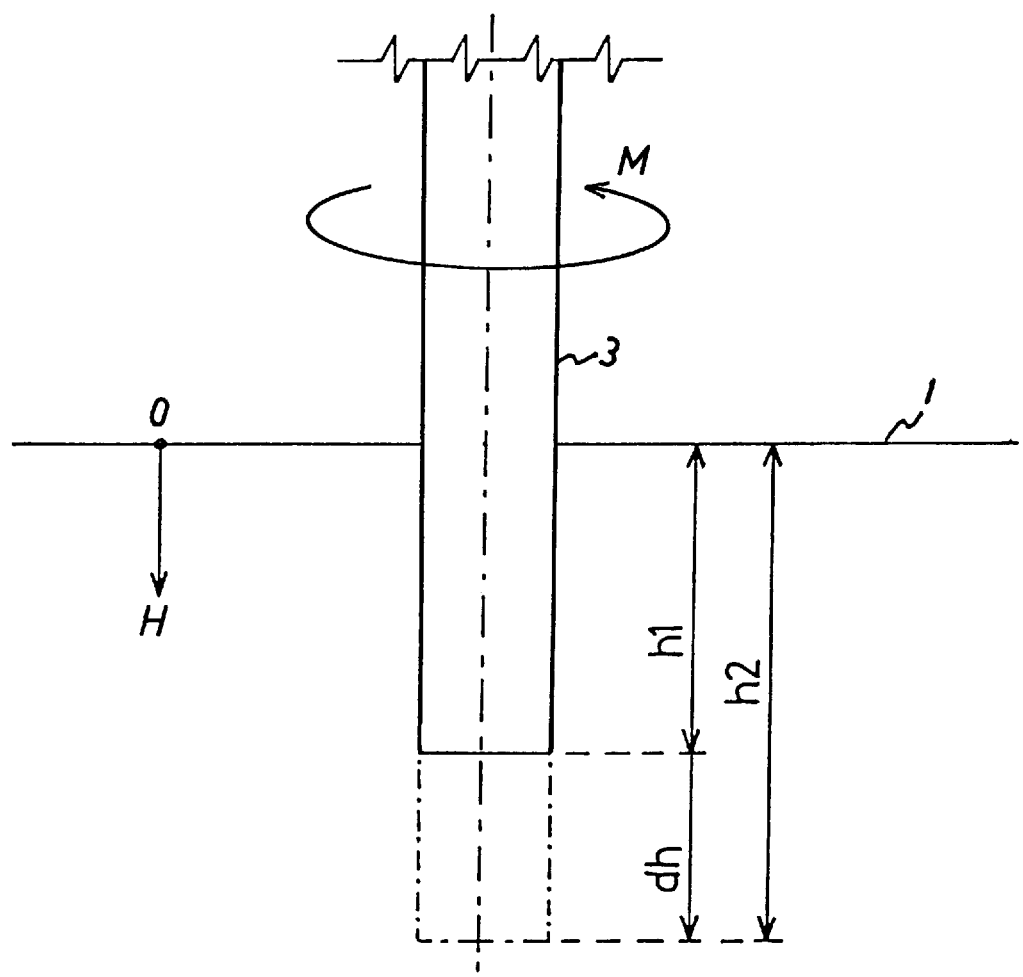
FIG. 4 schematically illustrates the free end of a measuring head according to the invention, and further indicates a few parameters used in the viscosity calculations involved in the method according to the invention.

A formula for calculating, in a manner known per se, the viscosity of a liquid on the basis of the torque values of a rotational viscosimeter takes into consideration the part torques transferred by the liquid to the measuring head from the sides and the underside (end) thereof. In addition, one takes into consideration the end effects occurring at the end of the measuring head. A formula of calculation for free-field measurement using a smooth rotating body of constant diameter in Newtonian fluid may read as follows.

$$M = \pi \cdot a^4 \cdot n \cdot \Omega \cdot (1 + \quad [1]$$
$$(1 \cdot 4 \cdot h)/(a^4 \cdot (1/a^2) - (1/b^2)) + \quad [2]$$
$$4 \cdot 1/a \cdot \Sigma(A_n \cdot I_2 \cdot n \cdot a/1) + \quad [3]$$
$$8 \cdot 1/(\pi \cdot a^2) \cdot \Sigma(B_n \cdot (\sinh(K_n \cdot h)/K_n)) \quad [4]$$

wherein M is the torque exerted by the liquid on the measuring head, $\Omega$ is the rotational speed of the measuring head, a is the radius of the measuring head, and h is the height of the measuring head.

The terms [3] and [4] illustrate the additional torque due to edge effects.

The viscosity n is obtained from the equation.

By using, in accordance with the invention, the difference between two torque values measured at two different positions in the liquid and then calculating the viscosity, one achieves a) that the measured difference in torque corresponds to the change in torque obtained upon a predetermined alteration of the depth of introduction into the liquid. In the short term, the other parameters, such as the rotational speed and the cross-section of the liquid, are maintained constant. In this manner, the difference in torque becomes a measure of the viscosity in the layer of the liquid located between the two measuring positions;

b) that the additional torque caused by edge effects can be subtracted in the calculation of the viscosity. The edge effects, i.e. the changes in torque caused by e.g. the side walls of a feeder channel, may be regarded as constant during the positioning of the measuring head. As long as the depth of introduction of the measuring head is altered but a small step in relation to the distance of the tip of the measuring head to the nearest wall, the error is negligible; and c) that the offset errors of the torque sensor, i.e. the deviations of the actual torque measured, are compensated for in the manner indicated under item b) above.

By using, in accordance with the invention, continuous positioning (introduction) of the measuring head, it becomes possible to d) calculate the viscosity with the aid of the differential of the torque value;

e) eliminate, in the manner indicated under item b) above, the cratering that arises when the measuring head breaks the surface of the liquid as a result of material being entrained by the measuring head during the positioning thereof, the cratering affecting the torque obtained from the measuring head; and f) obtain, with the aid of the second differential, a numerical value of the relative size of the change in viscosity, if any, over the cross-section through which the measuring head is moved.

With the aid of a device comprising a measuring head, which is moved in relation to the liquid during the measurement, it is possible to g) determine the viscosity of the liquid at several different points.

The above method, in which the change in torque during repositioning of the measuring head is used for calculating the viscosity, makes use of the following formula for a circular measuring head which is caused to rotate in the liquid:

$$M = C \cdot \int_0^h n(h)dh + \delta h \cdot n(h)$$

wherein M is the torque exerted on the measuring head, $\delta h$ is the change in the depth of introduction, h is the current depth of introduction, and C is a constant containing the number of revolutions (rotational speed) of the measuring head, as well as the diameter thereof.

The viscosity n is calculated for the part intervals dh and can be displayed for different depths of introduction, as well as for different points of time, if the measurements are carried out in order to monitor a liquid flowing past.

In one application where the viscosity is determined within an interval between two depths of introduction $h_1$ and $h_2$ by measuring the increase in torque at the upper and the lower limit of the interval, the viscosity can be obtained from the above formula as:

$$n(h_2) = M_3 - M_1/C \cdot (h_3 - h_1)$$

This example is drawn from an application where the measuring head is continuously positioned in (introduced into) the liquid, and the subscript 3 indicates the starting value for the calculations of the subsequent part interval.

There will now follow a brief description of a typical device for implementing the above measuring method in a process where a liquid flows past the device in an essentially continuous flow.

A liquid 1 (here melted glass) flows at a fairly constant speed through a feeder channel 2 which, in the drawing, is shown in a cross-section perpendicular to the direction of flow of the liquid 1.

In order to be rotated about its cylinder axis, a circular-cylindrical measuring head 3 is, via a shaft, connected to a driving motor 7, which in turn is connected to a casing 14. The driving motor 7 is connected to the casing 14 via a torque-sensing unit comprising a helical spring 8 and an angle transducer 9 in the form of a rotational velocity inductive transducer (RVIT).

The casing 14 is connected to a frame 4 via a control unit enabling linear displacement of the casing 14, and hence of the measuring head 3, and comprising a ball screw 5, which can be rotated by means of a step motor 6. A control unit 10 controls the step motor 6 and the driving motor 7 and samples measured values from the angle transducer 9.

The control unit 10 is connected to a computer (not shown) comprising programs for the control of the control unit 10, the reception of measured values and the calculation of viscosity values, and constituting an interface with respect to a user or to other equipment.

Conveniently, the measuring device is enclosed by an external cover having an inlet through which air for cooling the device can be introduced. The device is thermally insulated from the feeder channel 2 by means of an insulation 13.

When measuring and calculating the viscosity of the liquid, the measuring device operates as follows.

The measuring head 3 is at constant speed introduced axially down into the liquid 1. At an optional point $h_1$ for the end of the measuring head, a first torque $M_1$ is measured. Then, the measuring head 3 is continuously lowered axially in the h-direction until it reaches the depth of introduction $h_1+\delta h$, where a second torque $M_2$ is measured. The resulting change in torque, calculated as $M_2$ minus $M_1$, is divided by the change $\delta h$ in the depth of introduction. The quotient is multiplied by a constant containing the diameter and the rotational speed of the measuring head 3 with a view to determining a calculated viscosity value in the part interval $\delta h$.

It will be appreciated that the measuring head 3 is preferably so displaced that the liquid is wholly or partly penetrated, viscosity values being calculated for different part intervals. In addition, it is to be understood that the measuring head 3 may, if the temperature is to be measured at the different depths of introduction into the liquid, advantageously be combined with a temperature sensor (not shown) integrated at the free end of the measuring head 3.

We claim:

1. A method for measuring the viscosity of a liquid, wherein a rotary measuring head is introduced into the liquid, and the torque (M) exerted on the measuring head is sensed, characterized in that the measuring head is rotated at a substantially constant speed, that the torque (M) is sensed at two depths of introduction ($h_1$, $h_2$) of the measuring head into the liquid, and that the viscosity (n) of the liquid is calculated based on the formula:

$$M = C \cdot \int_0^h n(h)dh + \delta h \cdot n(h)$$

wherein M is the torque exerted on the measuring head,

C is a constant containing a rotational speed and diameter of the measuring head, h is the current depth of introduction, n is the viscosity of the liquid, and $\delta h$ is the change in the depth of introduction.

2. A method as set forth in claim 1, characterized in that the measuring head is introduced into the liquid at a substantially constant speed.

3. A method as set forth in claim 1, characterized in that the liquid is glass.

4. A viscosimeter for measuring the viscosity of a liquid, comprising:

a circular-cylindrical measuring head having a constant diameter and constructed to be rotated about its cylindrical axis;

an introduction mechanism which introduces the measuring head into the liquid;

a driving motor which is provided with a torque sensor and which rotates said measuring head;

a control unit that performs a measuring operation which causes said introduction mechanism to introduce the measuring head into the liquid along the cylindrical axis of the measuring head to at least two depths of introduction ($h_1$, $h_2$), causes said driving motor to rotate the measuring head at a substantially constant speed, and causes said torque sensor to sense torque (M) exerted on the measuring head at said at least two depths of introduction; and a calculation unit, connected to said control unit, which calculates the viscosity (n) of the liquid based on the formula:

$$M = C \cdot \int_0^h n(h)dh + \delta h \cdot n(h)$$

wherein M is the torque exerted on the measuring head,

C is a constant containing a rotational speed and diameter of the measuring head, h is the current depth of introduction, n is the viscosity of the liquid, and $\delta h$ is the change in the depth of introduction.

5. A viscosimeter as set forth in claim 4, characterized in that the free end of the measuring head is rounded or conical.

6. A viscosimeter as set forth in claim 4, characterized in that the measuring operation causes said introduction mechanism to introduce the measuring head into the liquid at a substantially constant speed along the cylindrical axis direction.

7. A viscosimeter as set forth in claim 4, characterized in that the liquid is glass.

* * * * *